US010241575B2

(12) United States Patent
Aksenova et al.

(10) Patent No.: US 10,241,575 B2
(45) Date of Patent: Mar. 26, 2019

(54) DIRECT NEURAL INTERFACE SYSTEM AND METHOD

(71) Applicant: COMMISSARIAT A L'ENERGIE ATOMIQUE ET AUX ENERGIES ALTERNATIVES, Paris (FR)

(72) Inventors: Tetiana Aksenova, Saint Egreve (FR); Andriy Yelisyeyev, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 356 days.

(21) Appl. No.: 15/032,546

(22) PCT Filed: Oct. 31, 2013

(86) PCT No.: PCT/IB2013/002725
§ 371 (c)(1),
(2) Date: Apr. 27, 2016

(87) PCT Pub. No.: WO2015/063535
PCT Pub. Date: May 7, 2015

(65) Prior Publication Data
US 2016/0282941 A1   Sep. 29, 2016

(51) Int. Cl.
*G05D 17/00* (2006.01)
*G06F 3/01* (2006.01)
(Continued)

(52) U.S. Cl.
CPC .......... *G06F 3/015* (2013.01); *A61B 5/04001* (2013.01); *A61B 5/04012* (2013.01);
(Continued)

(58) Field of Classification Search
CPC . G06F 3/015; A61B 5/04001; A61B 5/04012; A61B 5/0476; A61B 5/7203
(Continued)

(56) References Cited

U.S. PATENT DOCUMENTS

2003/0078738 A1* 4/2003 Wouters ................. G16H 10/20
702/22
2004/0073414 A1   4/2004 Bienenstock et al.
(Continued)

FOREIGN PATENT DOCUMENTS

WO   2011/144959 A1   11/2011

OTHER PUBLICATIONS

L. Hochberg et al., "Neuronal ensemble control of prosthetic devices by a human with tetraplegia," Nature, vol. 442, Jul. 13, 2006, pp. 164-171.
(Continued)

*Primary Examiner* — Connie C Yoha
(74) *Attorney, Agent, or Firm* — Baker & Hostetler LLP

(57) ABSTRACT

A direct neural interface system comprises: a signal acquisition subsystem for acquiring electrophysiological signals representative of neuronal activity of a subject's brain; and a processing unit for representing electrophysiological signals acquired over an observation time window in the form of a N-way data tensor, N being greater than or equal to two, and generating command signals for a machine by applying a regression model over the data tensor; wherein the processing unit is configured or programmed for generating command signals for a machine by applying Generalized Linear regression, with a nonlinear link function, over the data tensor. A method of interfacing a subject's brain to a machine by using such a direct neural interface system is provided.

15 Claims, 3 Drawing Sheets

(51) Int. Cl.
  *A61B 5/00* (2006.01)
  *A61B 5/04* (2006.01)
  *A61B 5/0476* (2006.01)
  *G06K 9/00* (2006.01)

(52) U.S. Cl.
  CPC .......... *A61B 5/0476* (2013.01); *A61B 5/7203* (2013.01); *G06K 9/00536* (2013.01)

(58) Field of Classification Search
  USPC ...................... 700/287; 702/179, 22; 606/33; 600/409, 516
  See application file for complete search history.

(56) References Cited

U.S. PATENT DOCUMENTS

| | | | |
|---|---|---|---|
| 2012/0209565 A1* | 8/2012 | Handley | G06F 3/121 702/179 |
| 2014/0236139 A1* | 8/2014 | Payman | A61B 18/18 606/33 |
| 2016/0073916 A1* | 3/2016 | Aksenova | A61B 5/7246 600/409 |
| 2018/0005105 A1* | 1/2018 | Schaeffer | G06N 3/0427 |

OTHER PUBLICATIONS

K. Shimoda et al., "Decoding continuous three-dimensional hand trajectories from epidural electrocorticographic signals in Japanese macaques," Journal of Neural Engineering, vol. 9 (2012), pp. 1-13.
Zenas C. Chao et al., "Long term asynchronous decoding of arm motion using electrocorticographic signals in monkeys," Frontiers in Neuroengineering, vol. 3, Mar. 30, 2010, XP002727291.

\* cited by examiner

DIRECT NEURAL INTERFACE SYSTEM AND METHOD

CROSS-REFERENCE TO RELATED APPLICATIONS

This application is a National Stage of International patent application PCT/IB2013/002725, filed on Oct. 31, 2013, the disclosures of which are incorporated by reference in their entirety.

FIELD OF THE INVENTION

The invention relates to a direct neural interface system, to a method of calibrating such a system and to a method of interfacing a subject's brain to a machine, e.g. a robotic arm.

Direct neural interface systems, also known as brain-computer interfaces (BCI) allow using electrophysiological signals issued by the cerebral cortex of a human or animal subject for driving an external device or machine. BCI have been the subject of intense research since the seventies. In 2006, a tetraplegic subject has been able to drive a robotic arm through a BCI. See the paper by Leigh R. Hochberg et al. "Neuronal ensemble control of prosthetic devices by a human with tetraplegia", Nature 442, 164-171 (13 Jul. 2006).

BACKGROUND

Until now, the best results in this field have been obtained using invasive systems based on intracortical electrodes. Non-invasive systems using electroencephalographic (EEG) signals have also been tested, but they suffer from the low frequency resolution of these signals. Use of electrocorticographic (ECoG) signals, acquired by intracranial electrodes not penetrating the brain cortex, constitutes a promising intermediate solution.

Conventional BCI systems use a limited number of "features" extracted from EEG or ECoG signals to generate command signals for an external device. These features can be related e.g. to the spectral amplitudes, in a few determined frequency bands, of ECoG signals generated by specific regions of the cortex when the subject imagine performing predetermined action. As a result, only a few features of the signal are used, while the other features of the signal are not taken into account. This approach is not completely satisfactory as, for any different command signal to be generated (e.g. vertical or horizontal movement of a cursor on a screen) it is necessary to identify different features, associated to different actions imagined by the subject and substantially uncorrelated from each other. Moreover, it is intrinsically inefficient as only a small amount of the information carried by the acquired ECoG signals is exploited.

The paper by Zenas C. Chao, Yasuo Nagasaka et Naotaka Fujii "*Long term asynchronous decoding of arm motion using electrocorticographic signals in monkeys*", Frontiers in Neuroengineering, Vol. 3, Art. 3, Mar. 30, 2010 describes a method of decoding (i.e. predicting) the motion of a monkey arm by applying PLS (Partial Least Squares) regression to wavelet-transformed ECoG signals. Such an approach allows a more efficient exploitation of the information carried by neuronal signals, and does not rely on predetermined "features" of said signals.

Document WO 2011/144959 discloses a BCI method wherein control signals for an external device or machine are generated by applying multi-way regression (e.g. N-way PLS, or NPLS) to neuronal signals represented as three-way tensors, said three ways corresponding to time, frequency and space. Use of multi-way instead of more conventional multiple regression (e.g. PLS) allows an even more efficient use of information.

Prior art BCI methods based on regression (either multilinear or multi-way) suffer from some drawbacks. Notably:
"Background" (non-task related) brain activity generates noise-like parasitic signals, which in turn generate spurious low-amplitude command signals. If the BCI is used e.g. to control a robotic arm, these spurious command signal induce a tremor of the arm in the absence of voluntary motion.
Muscular contraction (in particular, mastication) generates artifacts in the form of sharp peaks with large amplitude. If the BCI is used e.g. to control a robotic arm, these artifacts can induce large, unwanted motions.
Moreover, background brain activity and muscular artifacts are also suitable to "pollute" the data set used for learning the regression model used for command signal generation.

The paper of Kentaro Shimoda et al. "Decoding continuous three-dimensional hand trajectories from epidural electrocorticographic signals in Japanese macaques", Journal of Neural Engineering, Vol. 9, No. 3 discloses a method for detecting mastication artifact and eliminating them from the training data set of a regression model. However, this method cannot be applied "online" (in real time), during the application of the model.

SUMMARY OF THE INVENTION

The invention aims at overcoming at least some of the drawbacks of the prior art. More particularly, the invention aims at providing a BCI method and system which is at least partially immune from noise induced by background signal activity and/or muscular artifacts, while making efficient use of information carried by neuronal signals.

An object of the invention, allowing achieving this aim, is a direct neural interface system comprising:
a signal acquisition subsystem for acquiring electrophysiological signals $\underline{s}(t)$ representative of neuronal activity of a subject's brain; and
a processing unit for representing electrophysiological signals acquired over an observation time window in the form of a N-way data tensor, N being greater than or equal to one, and generating command signals for a machine by applying a regression model over said data tensor;
characterized in that said processing unit is configured or programmed for generating command signals for a machine by applying Generalized Linear regression, with a nonlinear link function, over said data tensor.

According to different embodiments:
Said processing unit may also be configured or programmed for detecting and correcting outlier elements of said data tensor before applying said Generalized Linear regression.
More particularly, said processing unit may be configured or programmed for generating command signals for a machine by applying Generalized Additive Linear regression over said data tensor, said Generalized Additive Linear regression making use of additive functions $f_i(x_i)$ of the form:

$$f_i(x_i) = \begin{cases} f_{1,i}(x_i) & \text{if } x_i \text{ is an outlier} \\ f_{2,i}(x_i) & \text{otherwise} \end{cases}$$

where $x_i$ is an element of said data tensor $\underline{x}(t)$ and $f_{1,i}$ and $f_{2,i}$ are different functions.

Even more particularly, said processing unit may be configured or programmed for generating command signals for a machine by applying Generalized Additive Linear regression over said data tensor, said Generalized Additive Linear regression making use of additive functions $f_i(x_i)$ of the form:

$$f_i(x_i) = \begin{cases} c_i & \text{if } x_i \text{ is an outlier} \\ x_i & \text{otherwise} \end{cases}$$

where $x_i$ is an element of said data tensor $\underline{x}(t)$ and $c_i$ is a constant.

Said processing unit may be configured to define said additive functions $f_i$ by applying a statistical test to a calibration dataset Said processing unit may be configured or programmed for representing electrophysiological signals acquired over an observation time window in a form chosen among: a 3-way data tensor $\underline{x}(t)$; or a vector $\underline{x}(t)$ corresponding to an unfolded 3-way data tensor; said three ways corresponding to time, frequency and space, Said processing unit may be configured or programmed for performing Generalized Linear regression based on PLS regression.

Said signal acquisition subsystem may comprise a plurality of ECoG or EEG electrodes.

Said processing unit may be configured or programmed for generating continuous command signals.

Another object of the invention is a method of interfacing a subject's brain to a machine comprising the steps of:
a) acquiring electrophysiological signals representative of neuronal activity of the subject's brain;
b) representing electrophysiological signals acquired over an observation time window in the form of a N-way data tensor $\underline{x}(t)$, N being greater than or equal to one; and
c) generating command signals for said machine by applying a regression model over said data tensor;
characterized in that said step c) comprises generating said command signals by applying Generalized Linear regression over said data tensor.

According to different embodiments:
The method may comprise a preliminary calibration step comprising: acquiring electrophysiological signals representative of neuronal activity of the subject's brain, and representing said electrophysiological signals acquired over at least one observation time window in the form of a N-way data tensor $\underline{x}(t)$, N being greater than or equal to one; acquiring at least one output vector y(t) associated to said time window or windows; determining a linear regression model between said data tensor or tensors and the corresponding output vector or vectors, and predicting at least on output vector $\hat{y}(t)$ from said linear regression model and at least one said data tensor; and determining, by nonlinear regression, a link function fitting said acquired output vector or vectors y(t) with corresponding predicted output vector or vectors $\hat{y}(t)$.

Said step c) may further comprise detecting and correcting outlier elements of said data tensor before applying said Generalized Linear regression.

Said step c) may be performed by applying Generalized Additive Linear regression over said data tensor, said Generalized Additive Linear regression making use of additive functions $f_i(x_i)$ of the form:

$$f_i(x_i) = \begin{cases} f_{1,i}(x_i) & \text{if } x_i \text{ is an outlier} \\ f_{2,i}(x_i) & \text{otherwise} \end{cases}$$

where $x_i$ is an element of said data tensor $\underline{x}(t)$ and $f_{1,i}$ and $f_{2,i}$ are different functions.

More particularly, said step c) may be performed by applying Generalized Additive Linear regression over said data tensor, said Generalized Additive Linear regression making use of additive functions $f_i(x_i)$ of the form:

$$f_i(x_i) = \begin{cases} c_i & \text{if } x_i \text{ is an outlier} \\ x_i & \text{otherwise} \end{cases}$$

where $x_i$ is an element of said data tensor and $c_i$ is a constant.

Said step c) may comprise a preliminary calibration step comprising defining define said additive functions $f_i$ by applying a statistical test to a calibration dataset.

Said step b) may comprise representing electrophysiological signals acquired over an observation time window in a form chosen among: a 3-way data tensor $\underline{x}(t)$; or a vector $\underline{x}(t)$ corresponding to an unfolded 3-way data tensor; said three ways corresponding to time, frequency and space, Said step c) may comprise performing Generalized Linear regression based on PLS regression.

Said step a) may comprise acquiring ECoG or EEG signals by using a plurality of spatially separated electrodes.

Said step a) may comprise generating continuous command signals.

BRIEF DESCRIPTION OF THE DRAWINGS

Additional features and advantages of the present invention will become apparent from the subsequent description, taken in conjunction with the accompanying drawings, which show.

DETAILED DESCRIPTION

Figure 1:
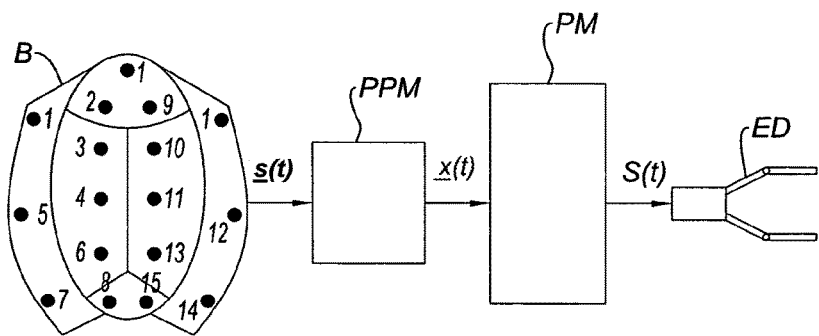
FIG. 1, a functional scheme of a direct neural interface system according to an embodiment of the invention.

FIG. 1 illustrates the general structure of a direct neural interface system according to an exemplary, and non-limiting, embodiment of the invention. In this embodiment, the cortex of the brain B of a human or animal subject is implanted with 32 measurement electrodes (to simplify the figure, only 14 are illustrated: references 2-15) and three reference electrodes (reference 1) for acquiring ECoG signals. As it is commonly known, the aim of these reference electrodes is to provide a "common signal". By "common signal", it is meant an electrical signal that affects all or most of measurement electrodes. As this signal is less specific to actions, it is usually preferable to evaluate it, as precisely as possible, so as to remove it. In this purpose, one or more reference electrodes may be operated. The ECoG signals acquired by the electrodes are pre-processed by a pre-processing module PPM.

Pre-processing comprises amplifying and filtering the raw signals acquired by the electrodes, sampling them e.g. at 1 kHz, converting the sample to digital format. In some embodiments, pre-processing may include subtracting a common signal measured by all electrodes.

The ECoG electrodes 1-15 and pre-processing module PPM form an acquisition subsystem, outputting a digital multichannel signal $\underline{s}(t)$.

Signal $\underline{s}(t)$ is then provided to a processing unit or module PM for generating command signals S(t) driving an external device or machine ED, e.g. a manipulator. Advantageously, command signals S(t) are "continuous", defining e.g. a three-dimensional trajectory of manipulator ED.

The pre-processing and processing modules can be implemented in the form of application-specific integrated circuits, programmable circuits, microprocessor cards, suitably programmed general-purpose computers, etc.

In the present exemplary embodiment of the invention, the method is applied for decoding the continuous three-dimensional hand trajectories from epidural ECoG signals of a Japanese macaque.

In their above-referenced paper "*Long term asynchronous decoding of arm motion using electrocorticographic signals in monkeys*", Zenas C. Chao and coworkers have recorded epidural ECoG signals of a Japanese macaque, and used them to decode (predict) continuous three-dimensional hand trajectories of the animal (hand motion was recorded by an optical motion capture signal with a sampling rate of 120 Hz). In the same time ECoG signals were recorded with a sampling rate of 1 kHz from 32 electrodes implanted in the brain.

In the present exemplary embodiment of the invention, the observed three-component hand trajectory signals are used to train the regression model, whereas the ECoG signals are used as input data.

Although the present exemplary embodiment is based on the hand movement of a monkey, the method could be used to acquire neuronal signal generated by the brain of a human subject imagining an action (e.g. moving an arm); then, a suitably trained regression model is used to generate—taking the neuronal signals as inputs—continuous command signals for a robotic arm, to make it follow the movement imagined by the subject.

A preliminary calibration step is necessary to build the regression model. This calibration step is carried out using a so called training set. This training step is followed by a step of model verification (so-called "test" step), using a so called test set. Train and test sets do not overlap.

During both calibration and test steps, features of recorded signals are extracted, so as to define a feature tensor $\underline{x}(t)$ from preprocessed signal $\underline{s}(t)$. Data (i.e. preprocessed ECoG signals) are subdivided into "time epochs", e.g. of 1 second duration; successive epochs have a temporal spacing of 0.2 s, therefore they overlap by 0.8 s. The signals of each epoch are mapped to time-frequency-space domain by continuous wavelet transform, e.g. by considering a frequency band from 5 to 300 Hz with 5 Hz steps. Due to the 1 kHz sampling rate, each time epoch initially includes 1000 time points.

At each frequency, the module of the wavelet-transformed signal is calculated. Further, a sliding average is applied, the size of the sliding windows being 100 ms. Then, a 10 times down sampling is carried out, so as to reduce the amount of time point data. As a result, each epoch is converted into a three-way tensor of dimension 60×100×32 (192,000 elements): 60 frequency bins, 100 time points, 32 channels, or electrodes.

During the calibration step, 1500 time epochs are considered. As a result, each time epoch-related feature tensor $\underline{x}(t)$ is gathered so as to form a fourth order calibration tensor $\underline{X}$.

The calibration tensor $\underline{X}$ is unfolded, which results in a matrix, each line of the matrix including an unfolded feature tensor $\underline{x}(t)$. In this case, during the test step, each feature tensor $\underline{x}(t)$ is further "unfolded" to form a vector (one-dimensional tensor) $\underline{x}(t)$.

The output vector $\underline{y}(t)$ includes the coordinates y(t) of the hand of the monkey at time t. During the calibration step, each $\underline{y}(t)$ vector corresponding to a given feature tensor $\underline{x}(t)$ is gathered to form a matrix Y. Therefore, the training data set includes:

$\underline{y}(t)$ vectors resulting from a tracking system which records the output variables, namely the hand coordinates; and $\underline{x}(t)$ feature tensors, corresponding to respective $\underline{y}(t)$ vectors.

The calibration step aims at determining a regression model between said output variables $\underline{y}(t)$ and said $\underline{x}(t)$ feature tensors.

According to the prior art, the regression model is linear multivariate and can be written:

$$E(y \mid \underline{x}) = \beta_0 + \sum_{i=1,p} \beta_i x_i \quad (1)$$

where:

E(·) represents the expected value of a random variable;

$\underline{x}$ is the unfolded feature tensor $\underline{x}(t)$, and $x_i$ with i=1–p (in the exemplary embodiment, p=192,000);

y is a coordinate of the output vector $\underline{y}$; and $\beta_0$, $\beta_j$, are constants, determined during the calibration step.

Alternatively, the calibration tensor may $\underline{X}$ not be unfolded, as described in WO2011144959. In this case, non-unfolded feature tensors also have to be used during the output vector calculation (i.e. trajectory decoding) step.

During the test step, the command signal S(t) is generated by applying regression model (1) to the feature tensors $\underline{x}(t)$ (more sophisticated approaches could use even higher-dimensional data tensors).

Figure 2:
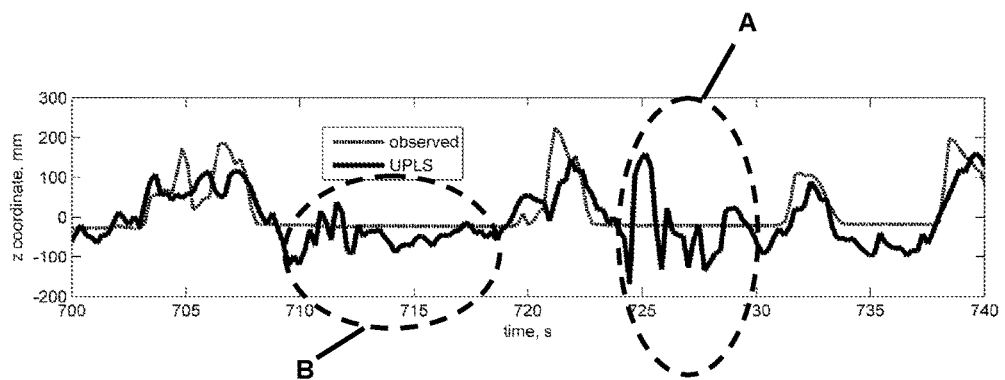
FIG. 2, a plot comparing an observed hand movement and its prediction by Unfolded PLS (UPLS) regression on ECoG signals, according to the prior art.

FIG. 2 has been obtained from the experimental data of Zenas C. Chao and coworkers (publicly available at http://neurotycho.org/epidural-ecog-food-tracking-task). The thin line represents the z-coordinate of the observed hand movement; the continuous line represents its reconstruction—which can be used as a command signal for a machine such as a robotic arm—obtained by applying unfolded PLS (UPLS) regression to epidural ECoG signals, preprocessed as discussed above, each time epoch being represented by a two-way tensor corresponding to the unfolding of a time-frequency-space three-way tensor. On FIG. 2, feature A represents an artifact due to mastication and feature B represents noise due to background brain activity. Therefore, the figure illustrates the above-mentioned drawbacks of the prior art.

The quality of the trajectory decoding (or "prediction") can be expressed by the correlation coefficients R, the normalized Absolute Mean Errors AME and the Absolute Mean Difference Errors AMDE. In the case of FIG. 2 one has:

$R_{UPLS}$=(0.51, 0.71, 0.67)
$AME_{UPLS}$=(26.6, 26.5, 47.6)
$AMDE_{UPLS}$=(20.1, 16.2, 32.7)

where values within brackets refers to x, y and z components of the hand trajectory (only the z-component being illustrated on the figure). The index "UPLS" reminds that PLS regression is used.

Actually, the FIG. 2 displays two sorts of noise:

The first type of noise is a high amplitude noise, which may be related non-brain specific activity. For example, it can be bodily muscular activity, such as mastication (see feature A on FIG. 2)

The second type is the brain background activity, i.e. non informative brain signal. (see feature B on FIG. 2)

An aim of the invention is to address these sorts of noises (or at least one of them), by the use of two different noise correction methods, so called Generalized Additive Model and Generalized Linear Regression which can be operated separately or combined.

According to an embodiment of the present invention, artifact due to non-brain activity (e.g. feature A on FIG. 2) can be corrected by:

Identifying components of each feature sensor which may be considered as outliers Correcting the previously identified outliers.

By outlier, it is meant a component of the feature tensor, which value is considered as not relevant with brain activity. Usually, outliers denote features which value exceeds a determined range.

From a mathematical standpoint, the proposed method is equivalent to replacing conventional multivariate linear regression—i.e. equation (1)—by a so-called linear Additive Model:

$$E(y \mid \underline{x}) = f_0 + \sum_{i=1,p} f_i(x_i) \quad (2)$$

with additive functions $f_i$ defined as:

$$f_i(x_i) = \begin{cases} f_{1,i}(x_i) & \text{if } x_i \text{ is an outlier} \\ f_{2,i}(x_i) & \text{otherwise} \end{cases} \quad (3)$$

$f_{1,i}$ and $f_{2,i}$ being different functions. In other words, a function f is applied on each feature $x_i$ of a feature tensor $\underline{x}(t)$, said function f being different whether said feature is considered as an outlier or not. In particular embodiments, the $f_{2,i}$ function may be constants, which can be determined during the calibration step, in which case (3) becomes:

$$f_i(x_i) = \begin{cases} c_i & \text{if } x_i \text{ is an outlier} \\ x_i & \text{otherwise} \end{cases} \quad (3')$$

Even more particularly, the constant $c_i$ may be equal to zero.

It is worth noting that additive functions $f_i$ are discontinuous, while, in the prior art, Additive Models most often use continuous and smooth additive functions.

There are several ways to identify outliers. For example, a statistical test can be performed based on the training data set. The distribution density of each feature $x_i$ can be estimated, the values exceeding a given threshold being then considered as outliers. The threshold can be predetermined, or calculated through statistical tests, such as the Grubb's test.

Figure 3:
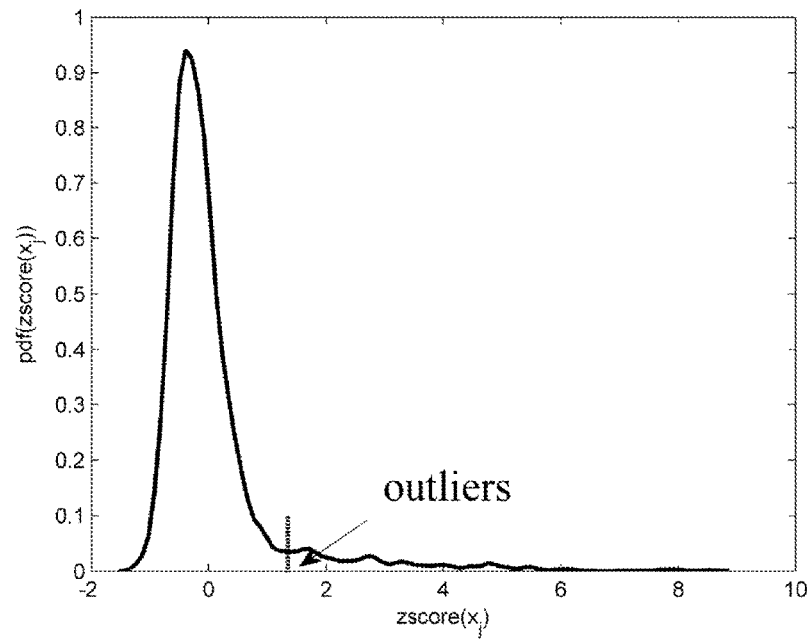
FIG. 3, a plot illustrating outlier detection in a method according to an embodiment of the invention.

FIG. 3 shows the plot of an exemplary probability density function (pdf) for an element, so called "zscore" of generic tensor element $x_j$ (j=1 . . . 192,000) and a threshold, determined by Grubbs' test, discriminating outliers from acceptable values. The term zscore denotes that the variable has previously been centered (mean value=0) and scaled (standard deviation=1). Anyway, data centering and scaling, prior to outlier identification, is optional.

Figure 4:
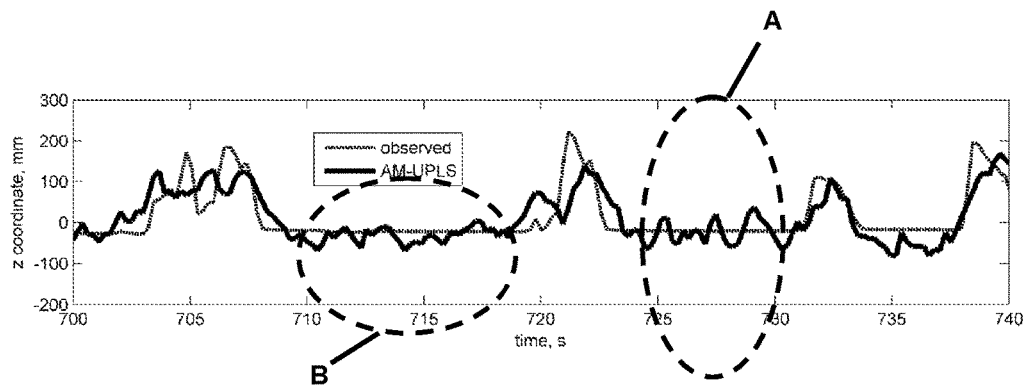
FIG. 4, a plot comparing an observed hand movement and its prediction by Additive Model—Unfolded PLS (AM-UPLS) regression on ECoG signals.

FIG. 4 shows the prediction of the z-component of the hand trajectory obtained using the Additive Model of equations (2) and (3) combined with UPLS regression (AM-UPLS). Experimental data are the same as in FIG. 2, and the dotted line corresponds to the z-component of the observed trajectory. It can be seen that artifact A has disappeared—being replaced by a much less intense noise-like disturbance. Moreover, noise B has been attenuated.

The values of R, AME and AMDE are as follows:
$R_{AM-UPLS}$=(0.57, 0.74, 0.76)
$AME_{AM-UPLS}$=(23.6, 22.1, 37.0)
$AMDE_{AM-UPLS}$=(15.0, 12.8, 24.5).

With respect to the conventional linear UPLS model used to obtain FIG. 2, R has increased and AME/AMDE decreased, which corresponds to an improvement of the quality of the prediction.

Although it also reduces noise, use of a linear Additive Model is primarily effective against muscular artifacts. A more effective way of dealing with noise, in particular induced by non-task related brain activity, is the use of a Generalized Linear Model (or Generalized Linear Regression model). As it is known in the art, in a Generalized Linear Model, a so-called "link function" (which is generally non-linear) is applied to the linear combination of predictor used in standard linear multivariate regression:

$$E(y \mid \underline{x}) = g\left(\beta_0 + \sum_{i=1,p} \beta_i x_i\right) \quad (4)$$

where $g(\cdot)$ is the nonlinear "link function".

Basically, the link function g takes into account, to some extent, the non-linear dependence between the predictors (i-e feature tensor $\underline{x}(t)$) and the response (i-e output) $\underline{y}(t)$.

Inventors have shown that the application of a link function, as previously defined, may significantly improve the reliability of the predicted vector. The link function g can be determined during the calibration step, as follows:

observed output vectors y(t) are extracted x(t) feature tensors, are measured, so that each feature tensor x(t) corresponds to an observed output vector y(t).

a first regression model between said output vectors y(t) and said x(t) features tensors is determined;

predicted output vectors ŷ(t) are computed using said first regression model, said predicted output vectors ŷ(t) are compared to the observed output vectors, and a link function g(ŷ(t)) is determined, preferably by nonparametric regression e.g. by Nadaraya-Watson kernel regression—which best fits said observed output vectors y(t) in other words the link function g is determined during a so called fit step, which aims at defining a link function g which, when applied to linearly predicted values best fits the observed values.

Said first regression model can be a linear regression model. In this case, $$\hat{y}(t) = \beta_0 + \sum_{i=1,p} \beta_i x_i(t).$$

Figure 5:
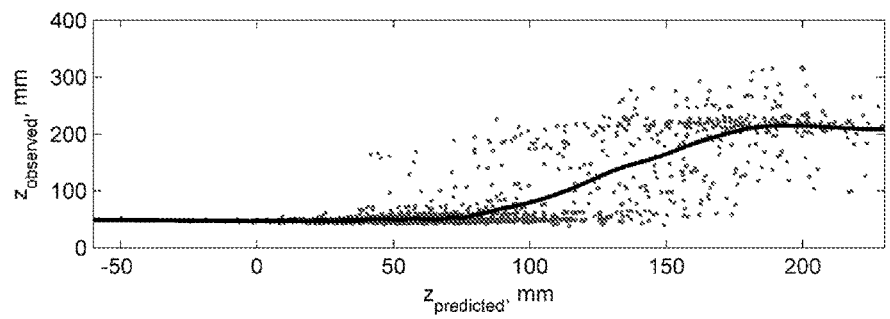
FIG. 5, a plot illustrating the determination of a link function used in a method according to an embodiment of the invention.

FIG. 5 shows a particular example of link function, obtained by taking linearly-predicted (i.e. predicted using linear PLS) values of z ($z_{predicted}$) as independent variables and observed values of z ($z_{observed}$) as dependent variables, "z" being the third coordinate of y. It can be seen that, in this particular case, for small values of $z_{predicted}$, g(z) is almost constant, thus suppressing low-amplitude noise; for high values of $z_{predicted}$, g(z) tends to a constant value, thus "clamping" high-amplitude peaks due to artifacts.

Figure 6:
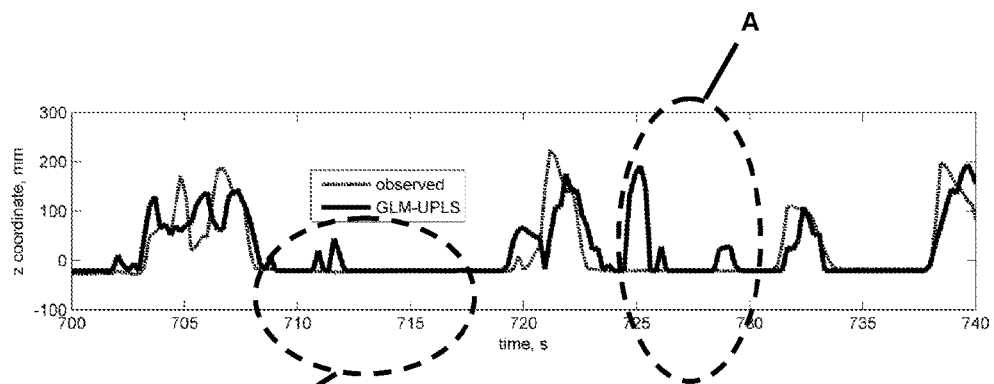
FIG. 6, a plot comparing an observed hand movement and its prediction by Generalized Linear Model—Unfolded PLS (GLM-UPLS) regression on ECoG signals.

FIG. 6 shows the reconstruction of the z-component of the hand trajectory obtained using the Generalized Linear Model of equation (4) combined with UPLS regression (GLM-UPLS). Compared to FIG. 2, it can be seen that the noisy feature B is quite effectively suppressed, and that even artifact A is somehow reduced (in particular by the suppression of unphysical negative values).

The values of R, AME and AMDE are as follows:
$R_{GLM-UPLS}$=(0.56, 0.76, 0.70)
$AME_{GLM-UPLS}$=(22.46, 17.1, 34.8)
$AMDE_{GLM-UPLS}$=(13.0, 12.6, 23.9).

In a preferred embodiment of the invention, both AM and GLM are combined with a linear regression method such as UPLS (Generalized Additive Model):

$$E(y \mid \underline{x}) = g\left(f_0 + \sum_{i=1,p} f_i x_i\right) \quad (5)$$

with additive functions $f_i$ given by equation (2) and a link function determined as discussed above.

Figure 7:
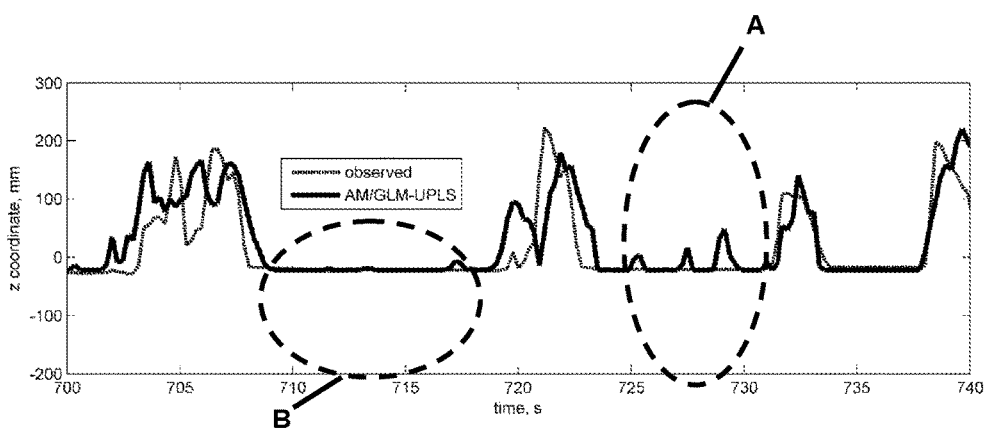
FIG. 7, a plot comparing an observed hand movement and its prediction by Generalized Additive Model—Unfolded PLS (AM/GLM-UPLS) regression on ECoG signals.

The technical result of this preferred embodiment is illustrated on FIG. 7.

The values of R, AME and AMDE are as follows:
$R_{AM/GLM}$=(0.66, 0.80, 0.79)
$AME_{AM/GLM-UPLS}$=(18.5, 15.5, 31.1)
$AMDE_{AMD/GLM-UPLS}$=(9.2, 10.0, 20.8).

It can be seen that noisy feature B is almost completely suppressed (which is not achieved by GLM-UPLS alone, not to speak of AM-UPLS alone), and artifact A is also significantly reduced (while AM-UPLS alone leaves a quite strong noise-like perturbation). This underlines the synergy between AM and GLM in BCI.

Equations (1), (2), (4) and (5) correspond to regression models for predicting one coordinate (z) of an arm trajectory. It will be easily understood that three separate models—and therefore three link functions in the case of GLM-UPLS and AM/GLM-UPLS and three sets of additive function in the case of AM-UPLS and AM/GLM-UPLS—are required for the complete prediction of the three-dimensional trajectory.

The invention has been described with reference to a specific, non-limiting embodiment using UPLS. However, any other known multivariable or multi-way linear regression method—of the PLS family or not—may be used.

In the exemplary embodiment described above, neuronal signals are represented by three-way (space, time, frequency) tensors obtained by continuous wavelet analysis of multichannel signals, which are subsequently unfolded. However, different N-way representation can also be used. Moreover, several different kind of signal preprocessing can be applied, as known in the art.

According to different embodiments of the invention, neuronal signals other than ECoG (e.g. EEG or intracortical signals) can be used to generate continuous or even discrete command signals, for a machine or external device which may not be a robotic arm.

The invention claimed is:

1. A direct neural interface system comprising:
a signal acquisition subsystem for acquiring electrophysiological signals s(t) representative of neuronal activity of a subject's brain; and
a processing unit for representing electrophysiological signals acquired over an observation time window in the form of a N-way data tensor (x(t)), N being greater than or equal to one, and generating command signals (S(t)) for a machine by applying a regression model over said data tensor,
wherein said processing unit is configured or programmed for generating command signals for a machine by applying Generalized Linear regression, with a nonlinear link function, over said data tensor,
wherein said processing unit is configured or programmed for detecting and correcting outlier elements of said data tensor before applying said Generalized Linear regression, and
wherein said processing unit is configured or programmed for generating command signals for a machine by applying Generalized Additive Linear regression over said data tensor, said Generalized Additive Linear regression making use of additive functions fi(xi) of the form:

$$f_i(x_i) = \begin{cases} f_{1,i}(x_i) & \text{if } x_i \text{ is an outlier} \\ f_{2,i}(x_i) & \text{otherwise} \end{cases}$$

where $x_i$ is an element of said data tensor x(t) and $f_{1,i}$ and $f_{2,i}$ are different functions.

2. A direct neural interface system according to claim 1, wherein said processing unit is configured or programmed for generating command signals for a machine by applying Generalized Additive Linear regression over said data tensor, said Generalized Additive Linear regression making use of additive functions fi(xi) of the form:

$$f_i(x_i) = \begin{cases} c_i & \text{if } x_i \text{ is an outlier} \\ x_i & \text{otherwise} \end{cases}$$

where $x_i$ is an element of said data tensor x(t) and $c_i$ is a constant.

3. A direct neural interface system according to claim 1, wherein said processing unit is configured to define said additive functions fi by applying a statistical test to a calibration dataset.

4. A direct neural interface system according to claim 1, wherein said processing unit is configured or programmed for representing electrophysiological signals acquired over an observation time window in a form chosen among:
   a 3-way data tensor x(t); or
   a vector x(t) corresponding to an unfolded 3-way data tensor, said three ways corresponding to time, frequency and space.

5. A direct neural interface system according to claim 1, wherein said processing unit is configured or programmed for performing Generalized Linear regression based on PLS regression.

6. A direct neural interface system according to claim 1, wherein said signal acquisition subsystem comprises a plurality of ECoG or EEG electrodes.

7. A direct neural interface system according to claim 1, wherein said processing unit is configured or programmed for generating continuous command signals.

8. A method of interfacing a subject's brain to a machine, the method comprising the steps of:
   a) acquiring electrophysiological signals (s(t)) representative of neuronal activity of the subject's brain;
   b) representing electrophysiological signals acquired over an observation time window in the form of a N-way data tensor x(t), N being greater than or equal to one; and
   c) generating command signals (S(t)) for said machine by applying a regression model over said data tensor;
   wherein said comprises generating said command signals by applying Generalized Linear regression over said data tensor,
   wherein said step c) further comprises detecting and correcting outlier elements of said data tensor before applying said Generalized Linear regression, and
   wherein said step c) is performed by applying Generalized Additive Linear regression over said data tensor, said Generalized Additive Linear regression making use of additive functions fi(xi) of the form:

$$f_i(x_i) = \begin{cases} f_{1,i}(x_i) & \text{if } x_i \text{ is an outlier} \\ f_{2,i}(x_i) & \text{otherwise} \end{cases}$$

where $x_i$ is an element of said data tensor x(t) and $f_{1,i}$ and $f_{2,i}$ are different functions.

9. A method according to claim 8, further comprising a preliminary calibration step comprising:
   acquiring electrophysiological signals (s(t)) representative of neuronal activity of the subject's brain, and representing said electrophysiological signals acquired over at least one observation time window in the form of a N-way data tensor x(t), N being greater than or equal to one;
   acquiring at least one output vector y(t) associated to said time window or windows;
   determining a linear regression model between said data tensor or tensors and the corresponding output vector or vectors, and predicting at least on output vector ŷ(t) from said linear regression model and at least one said data tensor; and
   determining, by nonlinear regression, a link function fitting said acquired output vector or vectors y(t) with corresponding predicted output vector or vectors ŷ(t).

10. A method according to claim 8, wherein said step c) is performed by applying Generalized Additive Linear regression over said data tensor, said Generalized Additive Linear regression making use of additive functions $f_i(x_i)$ of the form:

$$f_i(x_i) = \begin{cases} c_i & \text{if } x_i \text{ is an outlier} \\ x_i & \text{otherwise} \end{cases}$$

where xi is an element of said data tensor and $c_i$ is a constant.

11. A method according to claim 8, wherein said step c) comprises a preliminary calibration step comprising defining define said additive functions $f_i$ by applying a statistical test to a calibration dataset.

12. A method according to claim 8, wherein said step b) comprises representing electrophysiological signals acquired over an observation time window in a form chosen among:
   a 3-way data tensor x(t); or
   a vector x(t) corresponding to an unfolded 3-way data tensor,
   wherein said three ways correspond to time, frequency and space.

13. A method according to claim 8, wherein said step c) comprises performing Generalized Linear regression based on PLS regression.

14. A method according to claim 8, wherein said step a) comprises acquiring ECoG or EEG signals by using a plurality of spatially separated electrodes.

15. A method according to claim 8, wherein said step a) comprises generating continuous command signals.

* * * * *